United States Patent [19]

Matassa et al.

[11] Patent Number: 4,735,963

[45] Date of Patent: Apr. 5, 1988

[54] ANTI-PLATELET AGGREGATING 1,3-OXATHIANE DERIVATIVES, COMPOSITIONS, AND METHOD OF USE THEREFOR

[75] Inventors: Victor G. Matassa, Wilmington, Del.; Michael J. Smithers, Macclesfield, England

[73] Assignee: Imperial Chemical Industries PLC, London, England

[21] Appl. No.: 861,332

[22] Filed: May 9, 1986

[30] Foreign Application Priority Data

May 10, 1985 [GB] United Kingdom ............... 8511894

[51] Int. Cl.$^4$ ..................... A61K 31/39; C07D 327/06
[52] U.S. Cl. ...................................... 514/433; 549/14
[58] Field of Search ........................... 549/14; 514/433

[56] References Cited

FOREIGN PATENT DOCUMENTS 0094239 11/1983 European Pat. Off. ............. 549/375

OTHER PUBLICATIONS

Shimoji et al, Chemistry Letters, Chem. Soc. of Japan 1978, pp. 1375–1376.

Primary Examiner—Henry R. Jiles
Assistant Examiner—J. G. Mullins
Attorney, Agent, or Firm—Cushman, Darby & Cushman

[57] ABSTRACT

The invention concerns novel [5,6]-cis-1,3-oxathiane derivatives of formula I in which $R^1$ and $R^2$ are variously defined as hydrogen, alkyl, trifluoromethyl or phenyl (as set out in the specification), n is 1 or 2, m is 2, 3 or 4, Y is vinylene and Z is carboxy, 1(H)-tetrazol-5-yl or a group of the formula —CO.NH.SO$_2$R$^3$ in which $R^3$ is alkyl, phenyl or benzyl, and pharmaceutically acceptable salts thereof, for use in conjunction with their pharmaceutical compositions in treating certain pulmonary and/or vascular disorders. The invention also describes various processes and intermediates for the manufacture of the novel compounds.

10 Claims, No Drawings

ANTI-PLATELET AGGREGATING 1,3-OXATHIANE DERIVATIVES, COMPOSITIONS, AND METHOD OF USE THEREFOR

This invention concerns novel 1,3-oxathiane derivatives and, more particularly, novel (6-o-hydroxyphenyl-1,3-oxathian-5-yl)alkenoic acids and related compounds which antagonise one or more of the actions of thromboxane $A_2$ (hereafter referred to as "$TXA_2$") and which are of value as therapeutic agents.

It is known that $TXA_2$ is a potent aggregator of blood platelets and a powerful vasoconstrictor. $TXA_2$ is also a potent constrictor of bronchial and tracheal smooth muscle. $TXA_2$ may therefore be involved in a wide variety of disease conditions, for example ischaemic heart disease such as myocardial infarction, angina, cerebrovascular disease such as transient cerebral ischaemia, migraine and stroke, peripheral vascular disease such as atherosclerosis, microangiopathy, hypertension and blood clotting defects due to lipid imbalance, and pulmonary disease such as pulmonary embolism, bronchial asthma, bronchitis, pneumonia, dyspnoea and emphysema. Accordingly, compounds which antagonise the actions of $TXA_2$ may be expected to have therapeutic value in the prevention or treatment of any one or more of the above mentioned diseases or any other disease conditions in which it is desirable to antagonise the actions of $TXA_2$.

It is known from European patent application, publication No. 94239, that certain 4-phenyl-1,3-dioxan-5-ylalkenoic acids possess $TXA_2$ antagonist properties.

According to the invention there is provided a [5,6-cis]-1,3-oxathiane derivative of the formula I set out hereinafter wherein $R^1$ and $R^2$ are independently hydrogen, trifluoromethyl or (1-6C)alkyl, provided that $R^1$ and $R^2$ together contain no more than 6 carbon atoms; or $R^1$ is phenyl optionally bearing one or two substituents independently selected from halogeno, trifluoromethyl, cyano, nitro, (1-4C)alkyl and (1-4C)alkoxy, and $R^2$ is hydrogen; n is 1 or 2; m is 2, 3 or 4; Y is vinylene; and Z is carboxy, 1(H)-tetrazol-5-yl or a group of the formula $—CO.NH.SO_2.R^3$ wherein $R^3$ is (1-6C)alkyl, benzyl or phenyl, the latter two of which may optionally bear a halogeno, (1-4C)alkyl, (1-4C)alkoxy, nitro, cyano or trifluoromethyl substituent; or a pharmaceutically acceptable salt thereof.

It will be appreciated that the compounds of formula I contain at least two asymmetric carbon atoms (i.e. the carbon atoms at position 4 and 5 of the oxathiane ring) and may exist and be isolated in racemic and optically active forms. In addition, the compounds of formula I exist, in separate stereoisomeric forms ('E' and 'Z') about the vinylene group Y. It is to be understood that the present invention encompasses any racemic, optically active or stereoisomeric form, (or mixtures thereof), which is capable of antagonising one or more of the actions of $TXA_2$, it being well known in the art how to prepare individual optical isomers (for example by synthesis from optically active starting materials or resolution of a racemic form) and individual 'E' and 'Z' stereoisomers (for example by chromatographic separation of a mixture thereof), and how to determine the $TXA_2$ antagonist properties using the standard tests described hereafter.

Although a particular relative configuration is shown in the accompanying formulae, it is to be understood that this is not necessarily the absolute configuration.

A particular value for $R^1$ or $R^2$ when it is (1-6C)alkyl is, for example, methyl, ethyl, propyl, isopropyl, butyl or t-butyl.

Particular combinations of values for $R^1$ and $R^2$ together are, for example, $R^1$ is hydrogen, methyl, ethyl, isopropyl, t-butyl or trifluoromethyl and $R^2$ is hydrogen, methyl or trifluoromethyl; or $R^1$ is phenyl, optionally substituted as defined above, and $R^2$ is hydrogen.

A particular value for $R^3$ when it is (1-6C)alkyl is, for example, methyl, ethyl, isopropyl, propyl or butyl.

Particular values for optional substituents which may be present on $R^1$ or $R^3$ when it is phenyl, or for $R^3$ when it is benzyl, are, for example: fluoro, chloro or bromo, for halogeno; methoxy or ethoxy, for (1-4C)alkoxy; and methyl or ethyl, for (1-4C)alkyl.

In general m is preferably 2 or 3 and n is preferably 1.

Preferred values for $R^1$ and $R^2$ together include, for example: $R^1$ and $R^2$ are both hydrogen or methyl; $R^1$ is methyl, isopropyl, t-butyl or trifluoromethyl and $R^2$ is hydrogen; and $R^1$ is phenyl bearing a chloro, cyano, trifluoromethyl, nitro or methoxy substituent, and $R^2$ is hydrogen.

Y is preferably cis-vinylene.

A preferred value for Z is carboxy or a group of the formula $—CO.NH.SO_2.CH_3$.

Particular pharmaceutically acceptable salts of compounds of formula I are, for example, alkali metal and alkaline earth metal salts, such as lithium, sodium, potassium, magnesium and calcium salts, aluminium and ammonium salts, and salts with organic amines and quaternary bases forming physiologically acceptable cations, such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

Typical compounds of the invention are described in the accompanying Examples. Of these, the carboxylic acid described in Example 1, or a pharmaceutically acceptable salt thereof, is of especial interest.

The compounds of formula I may be manufactured by conventional procedures of organic chemistry well known in the art for the manufacture of structurally analogous compounds. Such procedures are provided as a further aspect of the invention and are illustrated by the following in which $R^1$, $R^2$, n, m, Y and Z have any of the meanings defined hereinabove:

(a) A phenol derivative of the formula II, wherein $R^4$ is a suitable protecting group, for example (1-6C)alkyl (such as methyl or ethyl), acyl (such as acetyl, benzoyl, methanesulphonyl or p-toluenesulphonyl), allyl, tetrahydropyran-2-yl or trimethylsilyl, is deprotected.

The precise deprotection conditions used depend on the nature of the protecting group $R^4$. Thus, for example, when it is methyl or ethyl the deprotection may be carried out by heating with sodium thioethoxide in a suitable solvent (such as N,N-dimethylformamide or 1,3-dimethyl-3,4,5,6-tetrahydro-2(1H)-pyrimidinone) at a temperature in the range, for example, 50°–160° C. Alternatively, an ethyl or methyl protecting group may be removed by reaction with lithium diphenylphosphide in a suitable solvent (such as tetrahydrofuran or t-butyl methyl ether) at a temperature in the range, for example, 0°–60° C. When the protecting group is acyl it may be removed, for example, by hydrolysis in the presence of a base (such as sodium or potassium hydroxide) in a suitable aqueous solvent [such as an aqueous (1–4C)alkanol] at a temperature in the range, for example, 0°–60° C. When the protecting group is allyl or tetrahydropyran-2-yl, it may be removed, for example, by treatment with strong acid such as trifluoroacetic acid and when it is trimethylsilyl, it may be removed, for example, by reaction with aqueous tetrabutylammonium fluoride or sodium fluoride, using a conventional procedure.

(b) For a compound of formula I wherein Z is carboxy, a compound of the formula I wherein Z is replaced by alkoxycarbonyl, phenoxycarbonyl, benzyloxycarbonyl, cyano or carbamoyl is hydrolysed.

A suitable value for Z, when it is alkoxycarbonyl, is methoxycarbonyl or ethoxycarbonyl.

The hydrolysis is generally performed using base catalysis, for example using an alkali meral hydroxide (such as lithium, sodium or potassium hydroxide) in a suitable aqueous solvent, for example a (1–4C)alkanol (such as methanol or ethanol) or a glycol (such as ethylene glycol) at a temperature in the range, for example, 0° to 150° C. In general, higher reaction temperatures, for example 80° to 150° C., are required when Z is cyano or carbamoyl.

It will be appreciated that the necessary hydrolysis conditions can also occur using process (a) hereinabove when a basic reagent is used to remove a (1–6C)alkyl or acyl protecting group. Consequently suitable starting materials for process (a) also include compounds of formula II in which Z is replaced by alkoxycarbonyl, phenoxycarbonyl, benzyloxycarbonyl, cyano or carbamoyl.

(c) An aldehyde of the formula III is reacted with a Wittig reagent of the formula IVa, IVb or IVc wherein R' is (1–6C)alkyl or aryl (especially phenyl) and M+ is a cation, for example an alkali metal cation such as the lithium, sodium or potassium cation.

The process in general produces predominantly those compounds of formula I in which the substituents adjacent to the double bond have cis-relative stereochemistry i.e. the 'Z' isomer. However, any of the analagous compounds of formula I having trans-relative stereochemistry about the double bond (i.e. the 'E' isomer) which may be produced in the process may be separated by crystallisation or chromatography of the initially formed mixture of cis-and trans-isomers.

The process may be conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, $-80°$ C. to 40° C., but may be conveniently performed at or near room temperature, for example in the range 0° to 35° C.

(d) For a compound of formula I wherein Z is 1(H)-tetrazol-5-yl, a nitrile of formula V is reacted with an azide.

A particularly suitable azide is, for example, an alkali metal azide such as sodium or potassium azide, which is preferably used together with an ammonium halide, for example ammonium chloride, ammonium bromide or triethylammonium chloride. The process is preferably carried out in a suitable polar solvent, for example N,N-dimethyl-formamide or N-methylpyrrolidone and, conveniently, at a temperature in the range, for example, 50° to 160° C.

The necessary starting materials for use in the above processes may be obtained by conventional procedures of organic chemistry, well known in the art for the production of structurally analogous compounds, for example, as disclosed in European patent applications, publication Nos. 94239, 142323 and 177121 and as illustrated in the accompanying Examples. Thus, the protected derivatives of formula II may be obtained, for example, as shown in Scheme I, and the aldehydes of formula III, for example, as shown in Scheme 2. In addition, the protected derivative of formula II (especially those wherein $R^4$ is acyl) may be obtained by carrying out process (c) above using an aldehyde of formula VI, in which case the deprotection step [process (a) above] may be conveniently carried out without isolation of the protected derivatives of formula II. The starting nitriles of formula V may be obtained, for example, by substituting the appropriate ylid of the formula $R'_3 P=CH.(CH_2)_m.CN$ for that of formula IVa-c in the Wittig reaction described in process (c) above.

The necessary Wittig reagents of formula IVa-c may be obtained by conventional procedures, for example by treating the corresponding phosphonium halides with a strong base, such as sodium hydride, lithium diisopropylamide, potassium t-butoxide or butyllithium. They are generally formed in situ just prior to carrying out the condensation process (c) above.

When a salt of a compound of formula I is required, it is obtained by reaction with the appropriate base affording a physiologically acceptable cation, or by any other conventional procedure.

Further, when an optically active form of a compound of formula I is required, one of the aforesaid processes may be carried out using an appropriate optically active starting material. Alternatively, the racemic form of a compound of formula I may be reacted with an optically active form of a suitable organic base, for example ephedrine, N,N,N-trimethyl-(1-phenylethyl-)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure for example using an aqueous mineral acid such as dilute hydrochloric acid.

Many of the intermediates defined herein are novel and are provided as further separate features of the invention. In addition, certain of the protected derivatives of formula II especially those wherein $R^4$ is methyl, n is 1, m is 2 or 3, and Y is cis-vinylene possess useful $TXA_2$ antagonist properties and are provided together with their pharmaceutically acceptable salts as a further feature of the invention.

As stated earlier, the compounds of formula I are antagonists of one or more of the actions of $TXA_2$, for example certain of its actions on blood platelets, the vasculature and/or the lung. The antagonism may be demonstrated in one or other of the following standard tests:

(a) The rabbit aortal strip model devised by Piper and Vane (*Nature*, 1969, 223, 29–35) using as agonist a freshly prepared sample of $TXA_2$, generated by addition of arachidonic acid (25 μg) to citrated, platelet rich rabbit plasma (250 μl) and allowing the mixture to aggregate fully over 90 seconds before use; alternatively the TXA$_2$ mimetic agent known as U46619 (described by R L Jones et alia, in "Chemistry, Biochemistry and Pharmacological Activity of Prostanoids" edited by S M Roberts and F Scheinmann, at page 211, Pergamon Press, 1979) may be used as the agonist;

(b) a blood platelet aggregation test based on that described by Born (Nature, 1962, 194, 927-929) and involving:

(i) aggregating human, citrated platelet-rich plasma by addition of the TXA$_2$ mimetic agent U46619 so that a dose-response curve is generated;

(ii) generating a dose-response curve for U46619 stimulated platelet aggregation in the presence of increasing amounts of test compound (generally in the range, $10^{-5}$M to $10^{-10}$M); and (iii) calculating a K$_B$ value indicating potency of TXA$_2$ antagonism for the test compound averaged over several concentrations, from the calculated 50% response value for U46619 aggregation in the presence and absence of test compound; and (c) a bronchoconstriction test involving measuring the inhibition by a test compound of the bronchoconstriction induced in the Konzett-Rossler, anaesthetised guinea-pig model (as modified by Collier and James, Brit. J. Pharmacol., 1967, 30, 283-307) by intravenous administration of the TXA$_2$ mimetic agent, U46619 and involving:

(i) obtaining a cumulative dose-response curve to U46619 induced bronchoconstriction by intravenous administration of constant volumes of increasing concentrations of U46619 (0.2-4 µg/kg) in physiological saline solution and expressing bronchoconstriction as the maximum of that theoretically obtainable with no air flow to the test animal;

(ii) generating a cumulative dose-response curve to U46619 induced bronchoconstriction at 30 minute intervals for 3 hours after oral dosing of test compound; and (iii) calculating a dose-ratio for the test compound (that is the ratio of concentration of U46619 required to cause 50% bronchoconstriction in the presence and absence of test compound) indicating the potency of TXA$_2$ antagonism.

The antagonism of the effects of TXA$_2$ on the vasculature may be demonstrated, for example, in rats in the following manner:

Male rats (Alderley Park strain) are anaesthetised with sodium pentobarbital and blood pressure is monitored at the carotid artery. The TXA$_2$ mimetic agent U46619 is administered intravenously via the jugular vein at 5 µg/kg to induce a 20-30 mm Hg (2640-3970 pascal) rise in systolic blood pressure. The process is repeated twice to establish the reproducibility of response to U46619. A test compound is then administered either intravenously (via the jugular vein) or orally (via a cannula directly into the stomach) and the animal challenged with U46619 five minutes after dosing with test compound and then successively every ten minutes until the hypertensive effect of U46619 is no longer blocked.

Further, the antagonism of the effects of TXA$_2$ in vivo may be demonstrated, for example, by assessing the effects of a test compound on the aggregation of blood platelets obtained after administration of test compound to a test animal such as a rabbit, rat, guinea pig or dog, using standard procedures similar to that described in (a) above. However, when the aggregation of dog platelets is being studied it is necessary to use a pre-determined, threshold concentration of the platelet aggregrant adenosine diphosphate (about 0.4-1.2×$10^{-6}$M) together with the TXA$_2$ mimetic agent, U46619.

As an illustration, the compound described in Example 1 has a pA$_2$ in test (a) of 7.42.

In general, compounds of formula I show significant TXA$_2$ antagonist properties in one or more of the above mentioned tests i.e. test (a) pA$_2$>6.0; test (b) K$_B$<5×$10^{-6}$; test (c) dose ratio>5 at 100 µg/kg p.o. In addition, compounds of formula I may show significant activity in the rat blood pressure test and/or in one or more of the ex vivo blood platelet tests referred to above. No significant adverse effects have been observed at the active doses in vivo.

As stated previously, the compounds of formula I may be used in the therapy or prevention of diseases or adverse conditions in warm-blooded animals in which it is desirable to antagonise one or more of the actions of TXA$_2$. In general, a compound of formula I will be administered for this purpose by an oral, rectal, intravenous, subcutaneous, intramuscular or inhalation route, so that a dose in the range, for example 0.1-5 mg/kg body weight, will be given up to four times per day, varying with the route of administration, the severity of the condition and the size and age of the patient under treatment.

The compounds of formula I will generally be used in the form of a pharmaceutical composition comprising a compound of formula I (or a pharmaceutically acceptable salt thereof) as defined hereinbefore, together with a pharmaceutically acceptable diluent or carrier. Such a composition is provided as a further feature of the invention and may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; and in the form of a powder together with one or more pharmaceutically acceptable inert solid diluents (such as lactose), for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents known to be of value in diseases or conditions intended to be treated; for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an antihistamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

In addition to their use in therapeutic medicine, the compounds of formula I are also useful as pharmacological tools in the development and standardisation of test systems for the evaluation of the effects of $TXA_2$ in laboratory animals such as cats, guinea pigs, dogs, rabbits, monkeys, rats and mice, as part of the search for new therapeutic agents. The compounds of formula I may also be used because of their $TXA_2$ antagonist properties in helping to maintain the viability of blood and blood vessels in warm-blooded animals (or parts thereof) under-going artificial extracorporeal circulation, for example during limb or organ transplant. When used for this purpose, a compound of formula I, or a physiologically acceptable salt thereof, will generally be administered so that a steady state concentration in the range, for example, 0.1 to 30 mg per liter is achieved in the blood.

The compounds of formula I are in general significantly more stable to acid than the comparable 1,3-dioxane derivatives described in European patent application, publication No. 94239.

The invention will now be illustrated by the following non-limiting Examples in which, unless otherwise stated:

(i) evaporations were carried out by rotary evaporation in vacuo;

(ii) operations were carried out at room temperature, that is in the range 18°–26° C.;

(iii) the progress of reactions was monitored by thin layer chromatography (TLC) on Merck 0.25 mm Kieselgel 60F 254 plates (Art. 5715); flash chromatography was performed on Merck Kieselgel (Art 9385), monitoring by TLC; these materials were obtained from E. Merck, Darmstadt, W. Germany;

(iv) yields are given for illustration only and are not necessarily the maximum attainable;

(v) NMR spectra were determined at 200 or 90 MHz (the latter indicated by an asterisk) in $CDCl_3$ using tetramethylsilane (TMS) as an internal standard, and expressed as chemical shifts (delta values) in parts per million relative to TMS using the following abbreviations for designation of major peaks: s, singlet; m, multiplet; t, triplet; br, broad; d, doublet; and (vi) end-products were isolated as racemates, and characterised by NMR, microanalysis, mass spectroscopy and/or other standard procedures.

EXAMPLE 1

Ethanethiol (0.85 ml) was added to a stirred suspension of sodium hydride (555 mg, 50% w/w dispersion in oil) in dry 1,3-dimethyl-3,4,5,6-tetrahydro-2-(1H)-pyrimidinone (DMPU) (10 ml) under argon. The mixture was stirred for 30 minutes. A solution of methyl 5(Z)-7-(2,2-dimethyl-6-o-methoxyphenyl-1,3-oxathian-cis-5-yl)heptenoate (547 mg) in DMPU (6 ml) was added and the mixture was heated to 130°–140° C. for 2 hours. Water (20 ml) was then added to the cooled reaction mixture. The aqueous mixture was washed with dichloromethane (20 ml). The aqueous layer was acidified to pH 4 with acetic acid and extracted with ethyl acetate (3×50 ml). The extracts were dried (MgSO₄) and evaporated. The residue was purified by flash chromatography eluting with ethyl acetate/hexane/acetic acid (50:50:1 v/v) to give 5(Z)-7-(6-o-hydroxyphenyl-2,2-dimethyl-1,3-oxathian-cis-5-yl)heptenoic acid, as an oil (505 mg); NMR: 1.5–1.85 (10H,m), 2.0–2.05 (2H,m), 2.25–2.3 (2H,m), 2.7–2.75 (1H,m), 2.9–3.0 (1H,m), 3.35–3.4 (1H,m), 5.15–5.4 (3H,m), 6.8–7.25 (4H,m), 7.4–8.4 (1H,br); m/e 351 (M+ +H).

The starting material was obtained as follows:

(i) A solution containing 5(Z)-7-(2,2-dimethyl-4-o-methoxyphenyl-1,3-dioxan-cis-5-yl)heptenoic acid (10.0 g), water (33 ml) and 2M hydrochloric acid (0.5 ml) in tetrahydrofuran (267 ml) was heated with stirring at 60°–70° C. for 2 hours. The solvent was then evaporated. The residue obtained was diluted with ether (350 ml). The mixture was washed with water (4×75 ml), then with saturated brine (2×75 ml), dried (MgSO₄) and evaporated. The oil obtained was purified by flash chromatography, eluting with toluene/ethyl acetate/acetic acid (60:40:2 v/v), to give 5(Z)-erythro-9-hydroxy-8-hydroxymethyl-9-o-methoxyphenyl-5-nonenoic acid (A) as a colourless oil, which slowly crystallised to give solid (8.4 g), m.p. 79°–80° C.; NMR (400 MHz): 1.66 (2H,m), 1.90 (1H,m), 2.08 (3H,m), 2.32 (3H,m), 3.69 (2H,m), 3.82 (3H,s), 5.22 (1H,d J=4 Hz), 5.37 (2H,m), 6.88 (1H,d J=8 Hz), 6.98 (1H,t J=7Hz), 7.25 (1H,m), 7.43 (1H,dd J=7, 2 Hz).

(ii) A solution of A (7.70 g) and ethyl acetate (10 ml) in ether (25 ml) was treated at 4° C. with an ice-cold ethereal solution of diazomethane until a yellow colour persisted. The solution was then treated with acetic acid (0.2 ml) and the solvent removed in vacuo. The residual oil was purified by flash chromatography, eluting with 45:55 v/v ethyl acetate/hexane, to give methyl 5(Z)-erythro-9-hydroxy-8-hydroxymethyl-9-o-methoxyphenyl-5-nonenoate (B) as a colourless oil (7.83 g); NMR (400 MHz): 1.74 (2H,m), 1.89 (1H,m), 2.05 (3H,m), 2.30 (3H,m), 2.47 (1H,br s), 3.13 (1H,d J=4 Hz), 3.66 (3H,s), 3.68 (2H,m), 3.84 (3H,s), 5.21 (1H,t J=4 Hz), 5.37 (2H,m), 6.88 (1H,d J=7 Hz), 6.99 (1H,t J=7 Hz), 7.2 (1H,m), 7.43 (1H,dd J=7, 2 Hz).

(iii) A solution of p-toluenesulphonyl chloride (5.27 g) in dichloromethane (25 ml) was added over 30 minutes to a stirred solution of B (7.68 g) in dichloromethane (50 ml) containing triethylamine (3.84 ml) maintained at 4° C. The mixture was then stirred for a further 1 hour at 4° C. and then for 64 hours at ambient temperature before being diluted with ether (200 ml). The subsequent mixture was washed successively with water (2×40 ml), 0.1M hydrochloric acid (40 ml), saturated brine (40 ml), 2% w/v sodium hydrogen carbonate solution (40 ml), water (2×40 ml) and then saturated brine (40 ml). The organic phase was dried (MgSO₄) and evaporated. The residual oil was purified by flash chromatography, eluting with first 25%, and then 35% and finally 50% v/v ethyl acetate/hexane to give methyl 5(Z)-erythro-9-hydroxy-9-o-methoxyphenyl-8-p-toluenesulphonyloxymethyl-5-nonenoate (C) as a colourless oil (8.56 g); NMR*: 1.97 (9H,m), 2.40 (3H,s), 3.60 (3H,s), 3.75 (3H,s), 3.95 (2H,m), 4.88 (1H,m), 5.23 (2H,m), 6.80 (2H,m), 7.18 (2H,m), 7.24 (2H,d J=8Hz), 7.65 (2H,d J=8Hz;).

(iv) Potassium thioacetate (6.85 g) was added to a solution of C (3.02 g) in dry dimethylsulphoxide (40 ml). The mixture was heated under argon at 60° C. for 1.5 hours. Saturated brine (100 ml) was then added and the mixture was extracted with ethyl acetate. The extracts (3×150 ml) were dried (MgSO₄) and evaporated. The residue was purified by flash chromatography, eluting with ethyl acetate/hexane (3:7 v/v) to give methyl 5(Z)-erythro-8-acetylthiomethyl-9-hydroxy-9-o-methoxyphenyl-5-nonenoate (D) as a yellow oil (2.15 g); NMR*: 1.5–2.4 (13H,m), 2.8–3.2 (2H,m), 3.65 (3H,s), 3.8 (3H,s), 4.9–5.0 (1H,m), 5.3–5.5 (2H,m), 6.8–7.4 (4H,m);

(v) Sodium methoxide (290 mg) was added to a solution of D (1.13 g) in argon-purged, dry methanol (45 ml)

and the mixture was stirred under argon for 1 hour. Saturated brine (30 ml) was then added and the aqueous mixture was extracted with ether (3×100 ml). The extracts were dried (MgSO4) and evaporated. The residue was dissolved in 2,2-dimethoxypropane (10 ml). p-Toluenesulphonic acid (5 mg) was then added. The mixture was stirred for 0.5 hours under argon and then heated at 60° C. for 1 hour. The cooled mixture was evaporated and the residue was purified by flash chromatography, eluting with ethyl acetate/hexane (1:4 v/v), to give methyl 5(Z)-7-(6-o-methoxyphenyl-2,2-dimethyl-1,3-oxathian-cis-5-yl)heptenoate as an oil (549 mg); NMR*: 1.5–1.7 (5H,m), 1.75 (3H,s), 1.9–2.05 (4H,m), 2.2–2.25 (2H,t), 2.65–2.8 (2H,m), 3.35–3.45 (1H,m), 3.65 (3H,s), 3.8 (3H,s), 5.1–5.3 (3H,m), 6.8–7.4 (4H,m).

EXAMPLE 2

Using a similar procedure to that described in Example 1, but starting from methyl 4(Z)-6-(6-o-methoxyphenyl-2,2-dimethyl-1,3-oxathian-cis-6-yl)hexenoate (E), there was obtained 4(Z)-6-(4-o-hydroxyphenyl-2,2-dimethyl-1,3-oxathian-cis-5-yl)hexenoic acid, as a colourless oil in 64% yield; NMR: 1.65 (3H,s), 1.75 (3H,s), 1.7–1.9 (2H,m), 2.2–2.4 (4H,m), 2.7–3.05 (2H,m), 3.3–3.45 (1H,m), 5.1–5.45 (3H,m), 6.8–7.2 (4H,m), 7.8–8.6 (2H,br); m/e: 337 (M+ +H).

The starting ester E was obtained as an oil in 33% yield, NMR*: 1.5–1.65 (4H,m), 1.75 (3H,s), 1.9–2.0 (1H,m), 2.2–2.3 (4H,m), 2.55–2.8 (2H,m), 3.35–3.45 (1H,m), 3.65 (3H,s), 3.8 (3H,s), 5.1–5.4 (3H,m), 6.8–7.45 (4H,m), using an analogous procedure to that described for the corresponding ester in Example 1, but starting from methyl 4(Z)-erythro-7-acetylthiomethyl-8-hydroxy-8-o-methoxyphenyl-4-octenoate (F). The ester F was itself obtained as follows:

(i) A solution of (4-o-methoxyphenyl-2,2-dimethyl-1,3-dioxan-cis-5-yl)acetaldehyde (15.8 g) in dry tetrahydrofuran (THF) (75 ml) was added under argon to an ice-cooled, stirred solution of the ylid prepared from (3-carboxypropyl)triphenylphosphonium bromide (51.48 g) and potassium t-butoxide (26.88 g) in dry THF (400 ml). The mixture was stirred, first for 15 minutes at 4° C. and then for 1.5 hours at ambient temperature. The mixture was added to ice/water (1 liter) and then washed with 50% v/v ether/hexane (2×250 ml) to remove neutral material. The aqueous phase was acidified to pH5 with acetic acid and extracted with ether. The combined extracts (3×300 ml) were dried (MgSO4) and evaporated. The residue was purified by flash chromatography, eluting with toluene/ethyl acetate/acetic acid (80:20:2 v/v) to give 4(Z)-6-(4-o-methoxyphenyl-2,2-dimethyl-1,3-dioxan-cis-5-yl)hexenoic acid (G) (13.04 g), m.p. 99°–101° C.; NMR: 1.52 (3H,s), 1.54 (1H,m), 1.56 (3H,s), 1.80 (1H,m), 2.28 (4H,m), 2.49 (1H,m), 3.77 (1H,dd J=11, 1 Hz), 3.82 (3H,s), 4.16 (1H,dm J=1 Hz), 5.28 (2H,m), 5.45 (1H,d J=2Hz), 6.83 (1H, dd J=7,1 1 Hz), 6.97 (1H, td J=7, 1Hz), 7.22 (1H,td J=8,1 Hz), 7.48 (1H,dm J=8 Hz).

(ii) Sodium hydroxide (6.16 ml of 25% w/v solution) was added to a stirred solution of G (8.43 g) in dry DMPU (50 ml). After 1 hour, iodomethane (8.5 ml.) was added and stirring continued for 3 hours. Saturated brine (100 ml) was then added and the mixture extracted with ethyl acetate (3×200 ml). The dried (MgSO4) extracts were evaporated and the residue purified by flash chromatography on silica, eluting with ethyl acetate/hexane (20:80 v/v) to give the methyl ester of G as an oil (7.5 g); NMR*: 1.4–1.9 (8H,m), 2.2–2.7 (5H,m), 3.65 (3H,s), 3.8 (3H,s), 4.0–4.25 (2H,m), 5.0–5.5 (3H,m), 6.75–7.5 (4H,m); m/e 349 (M+ +H).

(iii) 2M Hydrochloric acid (0.75 ml) was added to a solution of the methyl ester of G (7.5 g) in THF (140 ml) and water (30 ml). The mixture was heated under reflux in an argon atmosphere for 2 hours, cooled and treated with saturated brine (50 ml). The aqueous mixture was extracted with ether. The extracts were dried (MgSO4) and evaporated. The residue was purified by flash chromatography, eluting with ethyl acetate/hexane (50% v/v), to give methyl 4(Z)-erythro-8-hydroxy-7-hydroxymethyl-8-o-methoxyphenyl-4-octenoate (H), as a viscous oil (6.27 g); NMR*: 1.8–2.7 (7H,m), 2.8 (2H,br s), 3.6–3.8 (2H,m), 3.65 (3H,s), 3.85 (3H,s), 5.2–5.5 (3H,m), 6.8–7.55 (4H,m); m/e 309 (M+ +H).

(iv) A stirred mixture of triethylamine (3.1 ml), p-toluenesulphonyl chloride (4.27 g) and H (6.27 g) in dichloromethane (60 ml) was prepared at 0°–5° C. under argon. The mixture was stirred at ambient temperture for 52 hours and then evaporated. The residue was purified by flash chromatography, eluting with ethyl acetate/hexane (initially 30:70 v/v and then 50:50 v/v), to give methyl 4(Z)-erythro-8-hydroxy-8-o-methoxyphenyl-7-p-toluenesulphonyloxymethyl-4-octenoate as a viscous oil (I) (7.03 g); NMR*: 2.05–2.6 (10H,m), 3.65 (3H,s), 3.75 (3H,s), 3.7–4.15 (2H,m), 4.85–4.95 (1H,m), 5.1–5.4 (2H,m), 6.7–7.8 (8H,m).

(v) A solution of I in dimethylsulphoxide was reacted with potassium thioacetate at 60° C. under argon in an analogous manner to that described in part (iv) of Example 1. There was thus obtained methyl 4(Z)-erythro-7-acetylthiomethyl-8-hydroxy-8-o-methoxyphenyl-4-octenoate (F) in 91% yield as a viscous oil; NMR*: 1.9–2.6 (10H,m), 2.7–3.2 (3H,m), 3.7 (3H,s), 3.8 (3H,s), 4.9–5.0 (1H,m), 5.3–5.5 (2H,m), 6.8–7.5 (4H,m).

EXAMPLE 3

Ethanethiol (215 microliters) was added to a stirred suspension of sodium hydride (139 mg, 50% w/w dispersion in oil) in DMPU (5 ml) and maintained under argon. After 30 minutes, a solution of N-methanesulphonyl-5(Z)-7-(6-o-methoxyphenyl-2,2-dimethyl-1,3-oxathian-cis-5-yl)heptenamide (154 mg) in DMPU (3 ml) was added and the mixture was heated at 140° C. for 2.5 hours. Water (10 ml) was added to the cooled mixture which was then washed with methylene chloride (10 ml). The aqueous phase was acidified with acetic acid and extracted with ethyl acetate (3×30 ml). The extracts were dried (MgSO4) and evaporated. The residue was purified by flash chromatography, eluting with toluene/ethyl acetate/acetic acid (80:20:2 v/v) to give N-methanesulphonyl-5(Z)-7-(6-o-hydroxyphenyl2,2-dimethyl-1,3-oxathian-cis-5-yl)heptenamide as a viscous oil (49 mg); NMR*: 1.65 (3H,s), 1.8 (3H,s), 1.55–1.9 (4H,m), 1.95–2.1 (2H,m), 2.15–2.35 (3H,m), 2.65–2.8 (1H,dd), 2.8–3.0 (1H,m), 3.3 (3H,s), 3.35–3.45 (1H,m), 5.1–5.4 (1H,m), 6.8–6.95 (3H,m), 7.15–7.25 (1H,m); m/e 369 [M+—(CH3)2CO].

The starting material was obtained as follows:

(i) A solution of lithium hydroxide (7.5 ml of 0.5M aqueous solution) was added to a solution of methyl 5(Z)-7-(6-o-methoxyphenyl-2,2-dimethyl-1,3-oxathian-cis-5-yl)heptenoate (220 mg) in methanol (9 ml) and the mixture was stirred under argon for 16 hours. Saturated brine (15 ml) was added. The mixture was acidified with acetic acid and extracted with ethyl acetate (3×50 ml). The dried (MgSO4) extracts were evaporated and the residue purified by flash chromatography, eluting with ethyl acetate/hexane/acetic acid (30:70:1 v/v), to give 5(Z)-7-(6-o-methoxyphenyl-2,2-dimethyl-1,3-oxathian-cis-5-yl)heptenoic acid (J), as a viscous oil (175 mg); NMR: 1.5–1.65 (6H, m), 1.75 (3H,s), 1.9–2.1 (3H,m), 2.2–2.3 (2H,m), 2.65–2.8 (2H,m), 3.35–3.45 (1H,m), 3.85 (3H,s), 5.05–5.35 (3H,m), 6.8–7.45 (4H,m), 9.1–9.5 (1H,br s).

(ii) A solution of N,N'-dicyclohexylcarbodiimide (95 mg) in methylene chloride (5 ml) was added to a solution of J (168 mg), 4-(dimethylamino)pyridine (56 mg) and methanesulphonamide (44 mg) in methylene chloride (10 ml).

The mixture was stirred for 18 hours. The precipitated N,N'-dicyclohexylurea was removed by filtration, and washed with methylene chloride. The filtrate and washings were evaporated and the residue purified by flash chromatography, eluting with ethyl acetate/hexane/acetic acid (50:50:1 by v/v), to give N-methanesulphonyl-5(Z)-7-(6-o-methoxyphenyl-2,2-dimethyl-1,3-oxathian-cis-5-yl)heptenamide, as a viscous oil (172 mg); NMR: 1.45–1.7 (3H,m), 1.65 (3H,s), 1.75 (3H,s), 1.9–2.1 (3H,m), 2.2–2.25 (2H,m), 2.65–2.85 (2H,m), 3.3 (3H,s), 3.4–3.5 (1H,m), 3.8 (3H,s), 5.1–5.35 (3H,m), 6.85–7.45 (4H,m).

EXAMPLE 4

Illustrative pharmaceutical dosage forms include the following tablet and capsule formulations, which may be obtained using standard procedures:

| TABLET I | mg/tablet |
|---|---|
| Compound X* | 5.0 |
| Lactose Ph. Eur | 89.25 |
| Croscarmellose sodium | 4.0 |
| Maize starch paste (5% w/v paste) | 0.75 |
| Magnesium stearate | 1.0 |

| TABLET II | mg/tablet |
|---|---|
| Compound X* | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| CAPSULE | mg/tablet |
|---|---|
| Compound X* | 10 |
| Lactose Ph. Eur. | 488.5 |
| Magnesium stearate | 1.5 |

Note:
Compound X* stands for a compound of formula I, or a salt thereof, for example a compound of formula I described in any of the previous Examples.

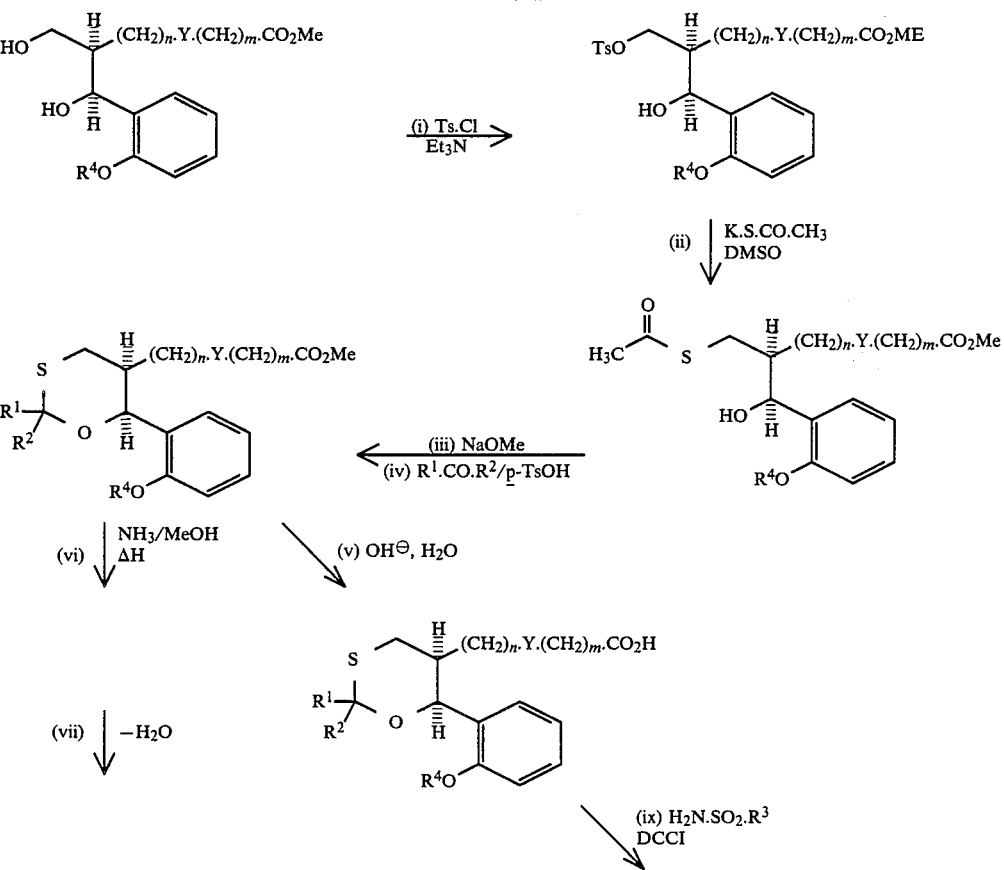

Scheme 1

4,735,963
-continued
Scheme 1
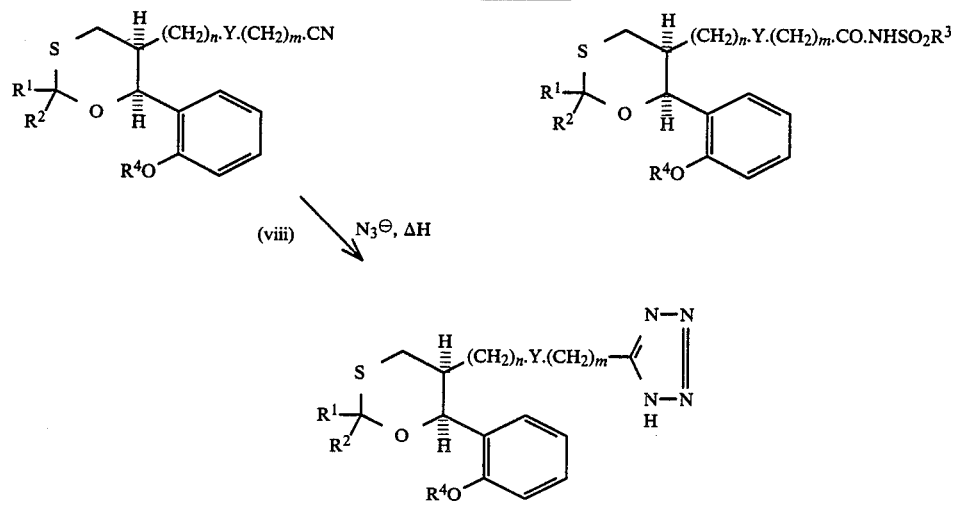
Ts = p-toluene.SO$_2$
Me = methyl
Et = ethyl
DCCI = dicyclohexylcarbodiimide
R$^4$ ≠ acyl
Scheme 2
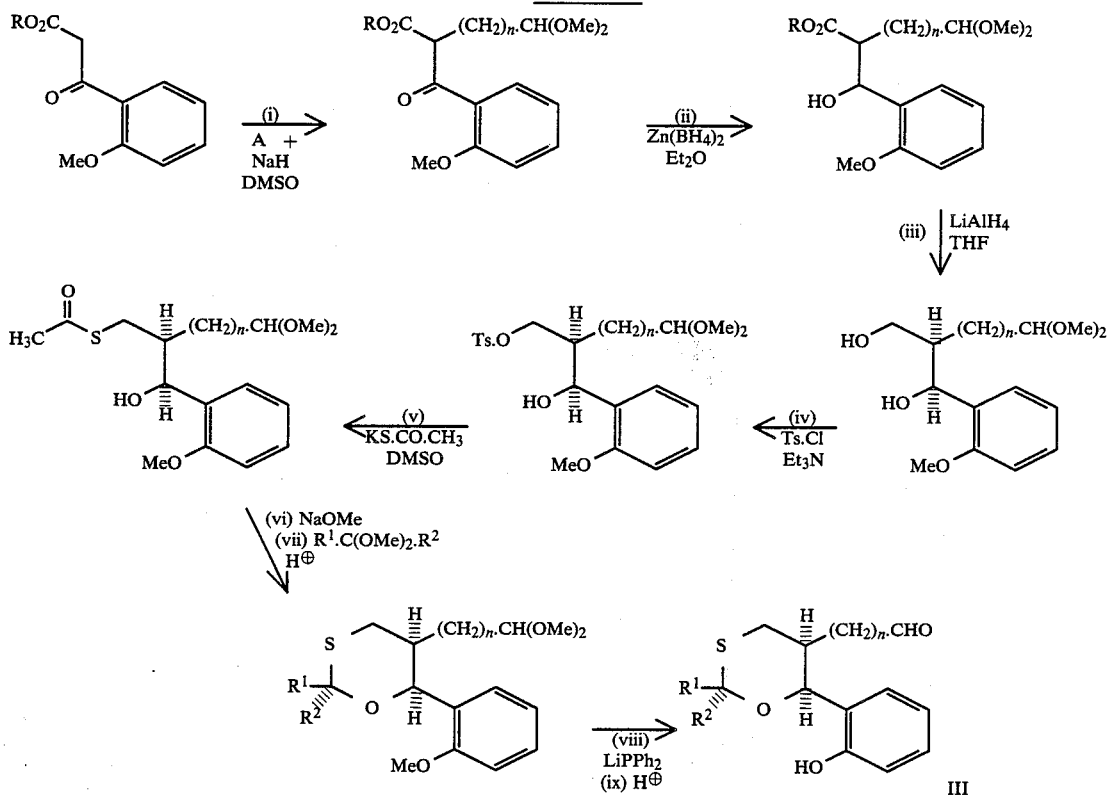
A = Br(CH$_2$)$_n$.CH(OMe)$_2$
Me = methyl
Ts = p-toluene.SO$_2$
Ph = phenyl Formulae

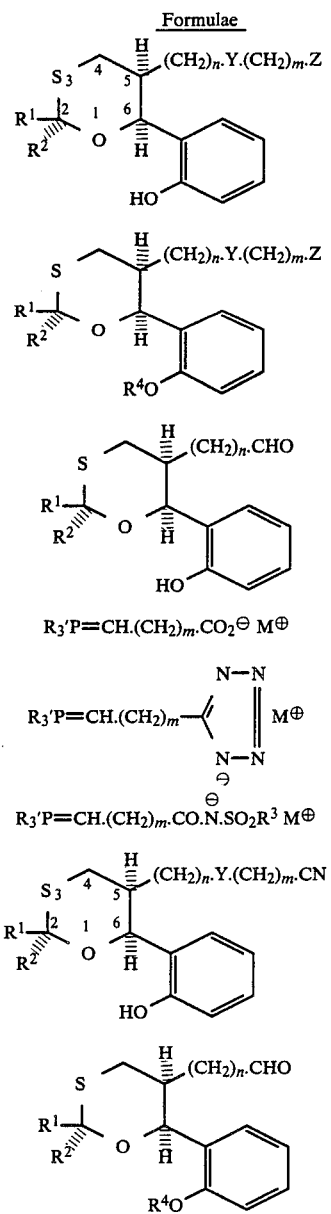

What is claimed is:
1. A [5,6]-cis-1,3-oxathiane derivative of the formula I

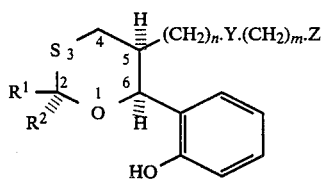

wherein $R^1$ and $R^2$ are independently hydrogen, trifluoromethyl or (1-6C)alkyl, provided that $R^1$ and $R^2$ together contain no more than 6 carbon atoms; or $R^1$ is phenyl optionally bearing one or two substituents independently selected from halogeno, trifluoromethyl, cyano, nitro, (1-4C)alkyl and (1-4C)alkoxy, and $R^2$ is hydrogen; n is 1 or 2; m is 2, 3 or 4; Y is vinylene; and Z is carboxy, 1(H)-tetrazol-5-yl or a group of the formula —CO.NH.SO$_2$.R$^3$, wherein $R^3$ is (1-6C)alkyl, benzyl or phenyl, the latter two of which may optionally bear a halogeno, (1-4C)alkyl, (1-4C)alkoxy, nitro, cyano or trifluoromethyl substituent; or a pharmaceutically acceptable salt thereof.

2. A compound as claimed in claim 1 wherein $R^1$ and $R^2$ are independently hydrogen, trifluoromethyl, methyl, ethyl, propyl, isopropyl, butyl or t-butyl, provided $R^1$ and $R^2$ together contain no more than 6 carbon atoms; or $R^1$ is phenyl optionally bearing one or two substituents independently selected from fluoro, chloro, bromo, methyl, ethyl, methoxy, ethoxy, trifluoromethyl, cyano and nitro, and $R^2$ is hydrogen; and $R^3$ is methyl, ethyl, propyl, isopropyl, butyl, benzyl or phenyl, the latter two of which may optionally bear a fluoro, chloro, bromo, methyl, ethyl, methoxy, ethoxy, trifluoromethyl, cyano or nitro substituent.

3. A compound as claimed in claim 1 or 2 wherein $R^1$ is hydrogen, methyl, ethyl, isopropyl, t-butyl or trifluoromethyl and $R^2$ is hydrogen, methyl or trifluoromethyl; or $R^1$ is phenyl optionally substituted as defined in claim 1 or 2, and $R^2$ is hydrogen.

4. A compound as claimed in claim 1 wherein Y is cis-vinylene, n is 1 and m is 2 or 3.

5. A compound as claimed in claim 1 wherein $R^1$ and $R^2$ are both hydrogen or methyl; $R^1$ is methyl, isopropyl, t-butyl or trifluoromethyl and $R^2$ is hydrogen; or $R^1$ is phenyl bearing a chloro, cyano, trifluoromethyl, nitro or methoxy substituent and $R^2$ is hydrogen; Y is cis-vinylene; n is 1; m is 2 or 3; and Z is carboxy or a group of the formula —CO.NH.SO$_2$.CH$_3$.

6. A compound selected from 5(Z)-7-(6-o-hydroxyphenyl-2,2-dimethyl-1,3-oxathian-cis-5-yl)heptenoic acid, 4(Z)-6-(6-o-hydroxyphenyl-2,2-dimethyl-1,3-oxathian-cis-5-yl)hexenoic acid, N-methanesulphonyl-5(Z)-7-(6-o-hydroxyphenyl-2,2-dimethyl-1,3-oxathian-cis-5-yl)heptenamide, and the pharmaceutically acceptable salts thereof.

7. A salt as claimed in claim 1 which is selected from from sodium, potassium, magnesium, calcium, aluminium and ammonium salts, and from salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

8. A method of antagonising platelet aggregation in a warm-blooded animal requiring such treatment which comprises administering to said animal an anti-platelet aggregation effective amount of a compound of formula I or a pharmaceutically acceptable salt thereof, as defined in claim 1.

9. A pharmaceutical composition which comprises an anti-platelet aggregating effective amount of a [5,6-cis]-1,3-oxathiane derivative of formula I, or a pharmaceutically accepatable salt thereof, as claimed in claim 1, together with a pharmaceutically acceptable diluent or carrier.

10. A compound of the formula II

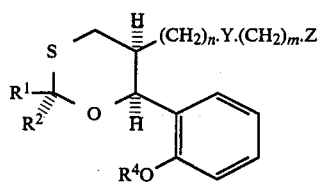
wherein $R^4$ is (1-6C)alkyl, n is 1, m is 2 or 3, Y is cis-vinylene, Z is carboxy and $R^1$ and $R^2$ have the meanings defined in claim 5, or a salt thereof.
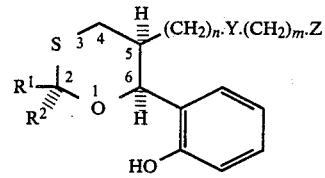
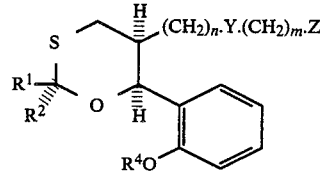
* * * * *